United States Patent [19]

Améen et al.

[11] 4,208,672
[45] Jun. 17, 1980

[54] METHOD AND APPARATUS FOR PRODUCING A COLOR THERMOGRAM ON PHOTOGRAPHIC FILM

[75] Inventors: Tore Améen, Upplands Väsby; Jan E. B. Dahlqvist, Akersberga, both of Sweden

[73] Assignee: Aga Aktiebolag, Lidingo, Sweden

[21] Appl. No.: 953,353

[22] Filed: Oct. 23, 1978

[30] Foreign Application Priority Data

Nov. 7, 1977 [SE] Sweden ................ 7712554

[51] Int. Cl.² ................ H04N 9/06; G02B 5/18; G03B 27/04
[52] U.S. Cl. ................ 358/6; 350/162 SF; 355/85
[58] Field of Search ................ 358/6, 54, 80; 355/35, 355/85; 350/162 SF

[56] References Cited

U.S. PATENT DOCUMENTS

| | | | |
|---|---|---|---|
| 2,736,761 | 2/1956 | Sziklai et al. | 358/6 |
| 2,983,784 | 5/1961 | Razdow | 358/6 |
| 3,647,943 | 3/1972 | Marshall | 358/6 |
| 4,087,176 | 5/1978 | Nigg | 358/6 |

Primary Examiner—Daryl W. Cook
Attorney, Agent, or Firm—Larson, Taylor and Hinds

[57] ABSTRACT

A method and apparatus are provided for producing a color thermogram on a color film beginning with images, such as those of a black and white television monitor, projected on the color film through color filters, with preferably three achromatic images being formed. The intensity of the achromatic color in each image as a function of temperature is selected in accordance with a predetermined characteristic or relationship and the images are projected through a color filter having a separate color for each image, e.g., blue, yellow and red. In this way the same portions of the image with achromatic colors which conform to the characteristic selected for the different filters are projected through the different filters, so as to produce a picture having color hues which vary between the colors of the filters. For example, a green hue is produced for an "overlap" of the characteristics for blue and yellow.

12 Claims, 13 Drawing Figures

METHOD AND APPARATUS FOR PRODUCING A COLOR THERMOGRAM ON PHOTOGRAPHIC FILM

The present invention relates to a method of producing a color thermogram on a photographic color film starting from images such as those of the screen of a black and white television monitor, projected on the color film through color filters and apparatus for carrying out the method.

It has long been known to produce with the aid of a black and white television picture screen, color thermograms on which different isotherms have been recorded, i.e. sections of a displayed heat-image representing a temperature lying between two given boundaries. An image for each isotherm is made light on an otherwise dark television screen, and is projected onto a color film via an individual color filter for each isotherm, which film is most often either a so-called miniature-camera film or a polaroid film. The latter is preferably used, since the thermogram is then obtained at once. If a relatively detailed thermogram with many isotherms is desired, as many exposures must be used with this method as the number of isotherms, while using just as many filters. This results in the mechanical arrangement being relatively clumsy and the recording of a thermogram taking a relatively long time to effect.

The different isotherms which are to be displayed on the television screen are provided by quantifying the video signal obtained from an infrared camera, the amplitude of this signal increasing with increasing temperature, which is represented by the signal. The signal is quantified in stages, where each stage represents signal sections between each of two selected boundary amplitudes in the video signal, and each portion of the video signal for each quantification step or stage being filtered out individually and displayed separately on the screen with full signal strength.

The reason that such a system with several exposures of a color film is often used instead of generating a color thermogram on a color television screen and taking colour photographs directly therefrom, is because the latter method requires a color television monitor, which is considerably more expensive than a black and white TV-monitor. IR-systems are often not compatible with television, i.e. they do not have the same line and picture frequency as the ordinary television system, and in such cases scanning converters and specially built monitors are required. In such cases in particular, color monitors are substantially more expensive than black and white monitors. The method using cheaper black and white monitors is therefore used in applications where there is not the need to monitor an instantaneous development of a heat sequence and where it is possible to wait for the time it takes for a picture to be ready, e.g. in medicine for certain routine investigations.

The above mentioned disadvantages with the earlier method are overcome by the method according to the invention.

The inventive method is based on the principle that in precisely the same way as different colors can be created by blending liquid pigments with each other to give the colors suitable hues, so can colors be mixed on a colour film by light of different colors being projected onto the film at different points in time or from different sources.

The invention will now be described in more detail with reference to the accompanying drawings, in which.

The invention is based on the principle that instead of generating an image on a black and white television picture screen where the light intensity on the screen increases with an increase in the temperature of the image, i.e. with more brilliant achromatic colors being produced for higher temperatures, images are generated where the light intensity, i.e. the achromatic color as a function of temperature, can be predetermined in accordance with a selected function or characteristic.

Figure 1A:
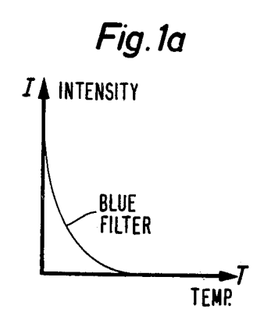
FIGS. 1a to 1c shows three different possible characteristics or functions of light or luminous intensity as a function of the object temperature for a generated achromatic color image on a television screen.
Figure 1B:
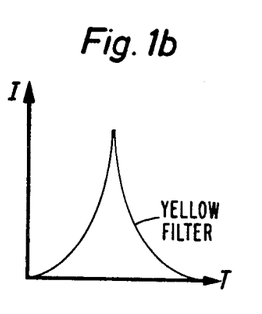
Figure 1C:
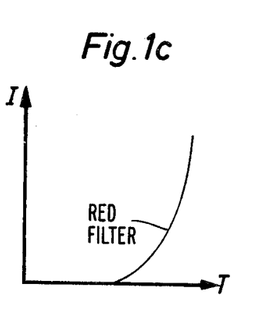

This principle can be utilized to provide color thermograms photographically with a considerably smaller number of exposures than the number of colors and hues on the finished film. All the colors variations between blue and yellow can be obtained on an exposed color film with only two functions and by using only two colour filters, e.g. an image with the light or luminous intensity function (intensity temperature characteristic) shown in FIG. 1a, exposed through a blue filter, and an image having the light or luminous intensity function shown in FIG. 1b, exposed through a yellow filter. Furthermore, if an image with the light intensity function shown in FIG. 1c is subsequently exposed through a red filter, there is obtained a range of colors from blue, green, yellow, orange to red, as will be clearly seen from FIG. 2, in which the three intensity functions have been plotted in the same diagram. This example shows how color thermograms with a wide colour spectrum can be produced using only two or three colors filters and a black and white television monitor. It should be pointed out that the intensity functions or characteristic curves shown in FIGS. 1a–1c are only to be regarded as examples of different functions which can be applied in this connection. As an example of a function combination, i.e., a combination of intensity-temperature characteristics, in which violet is also obtained for temperatures lower than the temperature represented by blue, the intensity functions shown in FIGS. 1a and 1c for red and blue can be varied in the manner illustrated by the combination in FIG. 3, which is analogous to that of FIG. 2. In FIG. 3, the function for red, in addition to the comparatively large part-function at higher temperatures, also contains a small part-function at the lowest temperatures which are to be indicated, and the shape of the curve for blue conforms with that for yellow but is displaced therefrom with relation to temperature.

Figure 2:
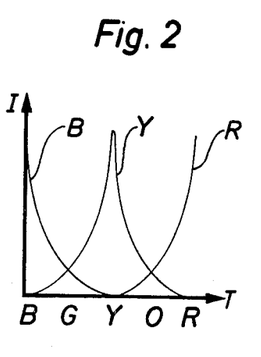
FIG. 2 shows a combination of functions according to FIG. 1.
Figure 3:
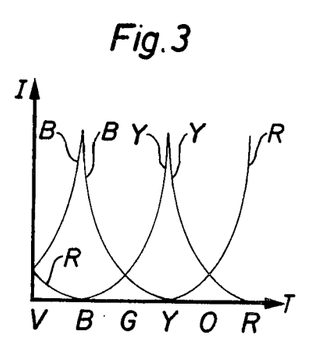
FIG. 3 shows a quantification of a straight line or linear function of the light intensity as function of the temperature of an achromatic color image.

By using the intensity functions shown in FIGS. 1–3 there is obtained a color thermogram with adjacent colors continuously merging into one another, the colors having the same color-sequence as the colors of the Spectrum, when the temperature passes from a low value to a higher one, i.e. blue or violet represents objects of low temperature and red represents objects of high temperature.

Figure 4A:
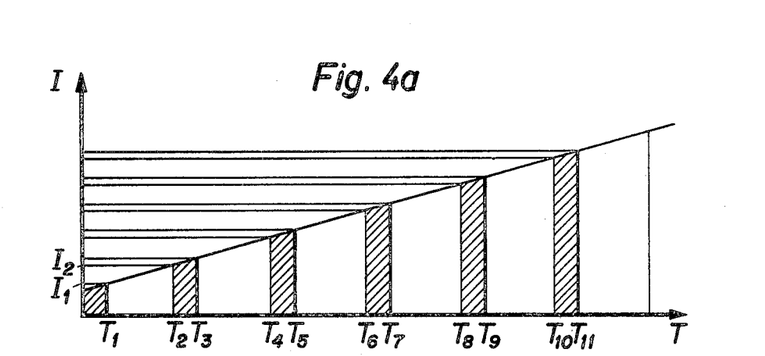
FIGS. 4a to 4e shows different configurations of intensity functions for obtaining the colors shown uppermost in the Figure through respective filters when exposing a color film.

If instead of having the colors merge with one another, it is desired to produce color thermogram with distinct colors for different isotherms, and also to place a black band between each isotherm, then quantification of a function obtained can be carried out where the intensity increases with increasing temperature. A linear function F with increasing intensity for increasing temperature is shown in FIG. 4a. Here it is desired, as is apparent from FIG. 4b, that of the respective temperatures section $T_1-T_2$ is yellow, $T_3-T_4$ is green, $T_5-T_6$ is orange, $T_7-T_8$ is red, $T_9-T_{10}$ is violet and $T_{11}-T_{12}$ is blue. In this embodiment the sequence has not been selected to conform with the colors in the Spectrum, as it was in the embodiments according to FIGS. 1-3, thereby emphasizing that colors can be selected in any suitable sequence. In this connection it should perhaps be pointed out that when recording thermograms, the most usual sequence of colors is black, blue-violet, blue, dark green, yellow-green, red-violet, red, yellow, and white, and that this color sequence will probably be used when the invention is applied in practice. It should be mentioned that the method according to the invention can readily be put into practice.

Figure 4B:
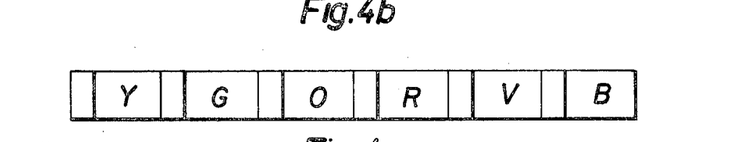
Figure 4C:
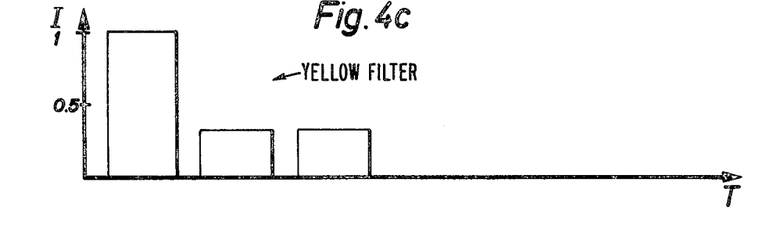
Figure 4D:
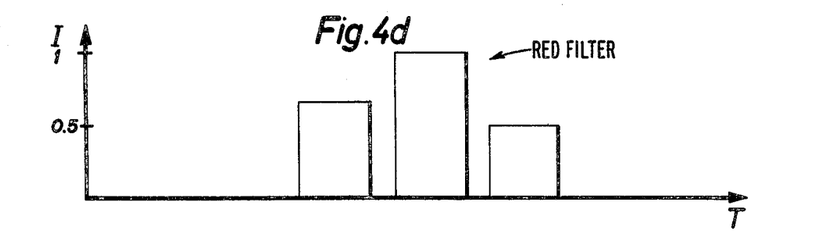
Figure 4E:
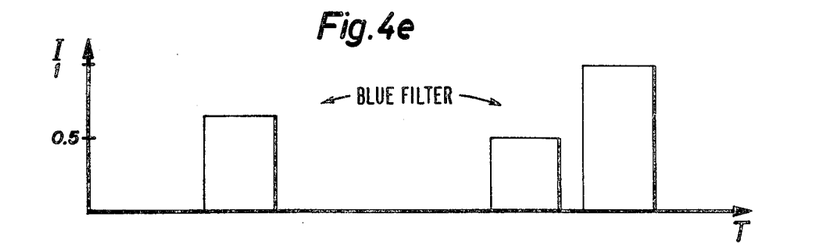

In FIGS. 4c–4e there are shown different configurations of the intensity-temperature functions for providing the colors shown in FIG. 4b by using the respective color filters when exposing a color film. It is previously known to separate different sections of the graph F individually, and that the signal within a given section can be amplified to the extent desired. This quantification can be performed in several different ways, of which the most usual is probably through the use of so-called window-comparators.

In accordance with the known method, one section is separated at a time, all those signal portions of the received video signal whose intensity lie between the intensities corresponded by the desired boundary temperatures (for example, the intensity range between the intensity levels $I_1$ and $I_2$ in FIG. 4a correspond to the temperature range between the boundary temperatures $T_1$ and $T_2$) are obtained separately and are amplified to full brilliancy or intensity on the television monitor screen. According to the embodiment of the invention described with reference to FIG. 4, several sections of the graph F are separated simultaneously instead, the signal portions for each section being amplified individually in conformation with a definite pattern, as is apparent from FIGS. 4c –4e. As these figures show, the sections for which the intensity is corresponded by the temperatures between $T_1$ and $T_2$, $T_3$ and $T_4$, $T_5$ and $T_6$ are separated for the achromatic color function of an image exposed by using a yellow filter. The portion of the signal corresponding to temperatures between $T_1$ and $T_2$ and which is to be shown by yellow is thereby amplified to maximum brilliancy or intensity on the monitor screen, whereas the portions of the signal corresponding to the temperatures between $T_3$ and $T_4$ (green), $T_5$ and $T_6$ (orange) are amplified for display on the monitor screen with an intensity corresponding to about $\frac{1}{3}$ of full intensity.

In the case of the achromatic color image which is to be projected onto the film through a red filter, there are separated out those sections whose intensity corresponds to the temperature ranges between $T_5$ and $T_6$, $T_7$ and $T_8$, $T_9$ and $T_{10}$, the signal portions in the first section, (which shall be reproduced in orange) being amplified so as to be displayed on the monitor screen with an intensity corresponding to $\frac{2}{3}$ of full intensity, the second section (for showing with red) being amplified for display with full intensity and the signal portions in the third section for display at half intensity.

In the case of the achromatic color image which is to be projected onto the film through a blue filter, there are separated out those sections whose intensity corresponds to the temperature ranges between $T_3$ and $T_4$, $T_9$ and $T_{10}$, $T_{11}$ and $T_{12}$. The signal portions in the first section which shall be reproduced in green are amplified so as to be displayed on the monitor screen with an intensity corresponding to $\frac{2}{3}$ of maximum, the signal portions of the next said section which shall be reproduced in violet are amplified for display at one-half of the full intensity and the signal portions in the last mentioned section are amplified to be reproduced at full intensity.

By this method there is provided, additional to the pure color of the filters, additive color mixtures of the filter color in accurately balanced proportions, which can be determined separately and individually. In this connection it should also be emphasized that the filters used need not be adapted to allow light of the same strength to pass therethrough, and a difference here can naturally be compensated by the intensity of the image displayed on the screen in each individual case.

If a black band is desired between each field of color in the image, a small zone can be kept free between the quantified ranges, i.e. the spaces between $T_2$ and $T_3$, $T_4$ and $T_5$, $T_6$ and $T_7$, $T_8$ and $T_9$, $T_{10}$ and $T_{11}$ in FIG. 4a. It is also conceivable for the width of each quantified range to be variable. If both the original intensity function, i.e. the linear graph F, is displaceable and the width of the quantified ranges is variable, color thermograms can be obtained in which the temperature of an area can be very accurately determined.

Figure 5:
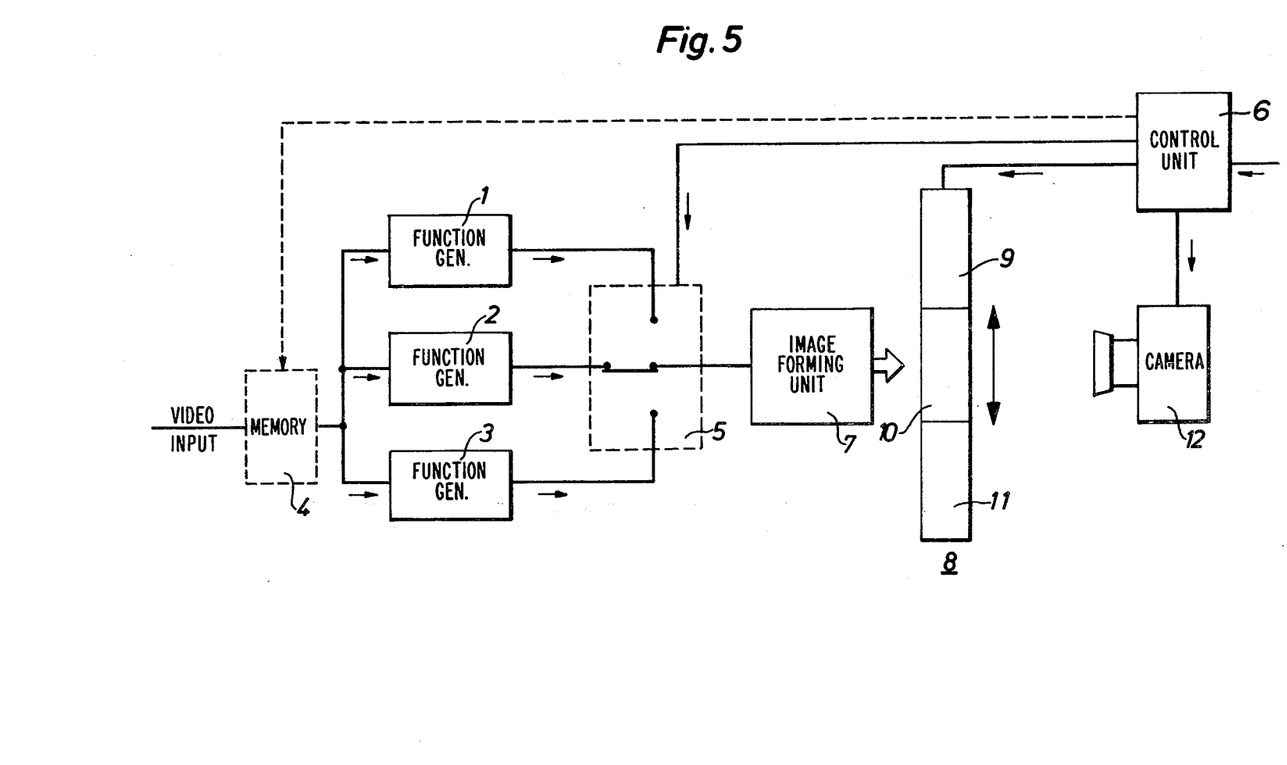
FIGS. 5, 6 and 7 show different embodiments of circuits for carrying out the method according to the invention.

FIG. 5 is a block schematic of one embodiment of a circuit by which the method according to the invention can be carried out. A video signal from an IR-camera is fed in parallel to three function generators 1, 2 and 3, each of which converts the input signal having a linear temperature-intensity function to a temperature-intensity function signal of some other suitable configuration. This embodiment is especially suitable for carrying out the embodiment of the invention described with reference to FIGS. 1-3, wherein the function generators are analogue, but may also be used with the embodiment described with reference to FIG. 4, in which case each function generator is provided with a quantifier.

Image generators of the type described here are often used for registering relatively slow sequences of events. In earlier systems with one exposure per thermogram, the method could be used when it was expected that the reproduced object or temperature variation did not alter substantially during a time interval of about 15 seconds, which interval could have been reduced to about 3 seconds by using the invention. In this case the video signals are taken by continual scanning of the object and fed directly to the inputs of the function generators.

The outputs of the function generators 1–3 are each connected to a switch 5, preferably an electronic switch, which selectively couples the output signal from one of the function generators 1–3 to an image-forming unit 7. The particular function generator connected to the unit 7 depends upon which color filter is, at that moment, placed in front of the screen of the unit, and this function generator is selected by actuating a control unit 6 connected to the control input of the switch 5.

As is apparent from FIG. 3, some of the intensity-temperature functions which are to be provided by the function generators can, in certain cases, have the same form but be displaced in amplitude with relation to the incoming signal, i.e. the graph applicable for exposure using a blue filter for showing comparatively low temperatures can have the same form as the graph applicable for exposure using a yellow filter for showing relatively high temperatures. In this case, although the same function generator can be used, it will be understood that it is necessary to ensure that the generator can be switched between two or three basic amplitude levels as applicable.

The image forming unit is preferably a black and white TV-monitor. The image on the screen of the unit is projected through one of the filters in a filter unit 8 which is controlled by means of the control unit 6. The filter unit 8 is shown in FIG. 5 as comprising three filter parts 9, 10, 11, and the control unit controls a motor which either moves the filter adapted for the selected function generator into position in front of the image forming unit, when the filters are arranged in a row as shown in FIG. 5, or rotates the filter unit 8 so that the appropriate filter comes into position for an embodiment wherein the filters are arranged in a circle on a rotatable unit. The control unit 6 sends a control signal to the switch 5 and to the filter unit 8 simultaneously. After a suitable time lapse, the control unit energizes a camera unit 12 which takes a picture of the screen of the image-forming unit 7, through the particular filter 9, 10 or 11 located in front of the screen.

As is shown in FIG. 5, the control unit 6 is activated by an operator, whereafter it can be programmed to carry out the whole of the operation cycle automatically with three settings of the switch 5 and the filter unit 8. It is also conceivable to replace the control unit 6 with an operator, i.e. an operator who would manually operate the switch 5, filter unit 8 and camera 12.

In FIG. 5 there is also shown (in dashed lines) a storage element or memory 4, which can be used in the case where it is desired to register the temperature of a rapidly moving object or the instantaneous temperature of an object with rapid temperature variations. In this case, a video signal relating to an image surface is stored in the storage element or memory 4 and the content of the memory is read once for each of the different exposures. Where analogue registration is used, as in accordance with the embodiment illustrated in FIGS. 1–3, the memory 4 is of an analogue type. Memory 4 can, for example, take the form of a CCD-type shift register. Since information concerning an entire image surface must be stored, control equipment pertaining to the memory will be relatively large and thus expensive, but it should be observed that the temperature of extremely rapidly moving objects can readily be registered with apparatus provided with such a memory. When picking up the video signal, it is namely preferably to pick up the lines in the image one after the other in sequence instead of taking up alternate lines in a first step and the remaining lines in a second step. Such an arrangement is very easy to provide, since it is only a question of allowing the vertical deflection unit, e.g. a vertical deflection prism, to move at half the normal speed and to take up only the scan from one vertical deviation. The same then also applies to the recording on the screen of the image forming unit. Although it is true that if the object is moving extremely quickly, its image can be a trifle deformed, since the image has time to move a short distance between the recording of each line, the image obtained will nevertheless be sharp, and the temperatures in the different parts of the image clearly discernible.

Figure 6:
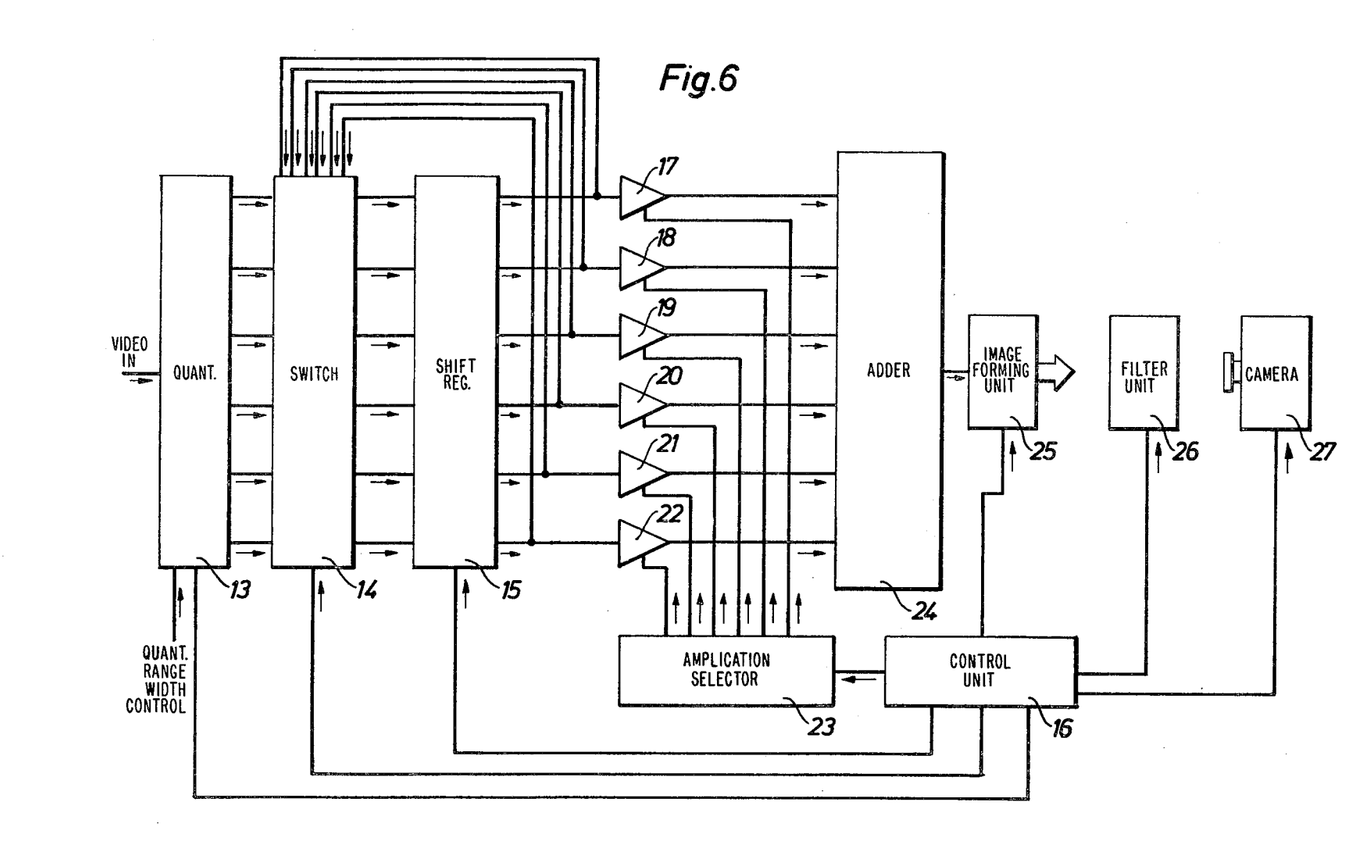

FIG. 6 is a block schematic of another embodiment of a circuit with which the embodiment of the method described with reference to FIG. 4 can be carried out. The circuit of the FIG. 6 embodiment is designed to enable rapid sequences to be registered. The video signal from an IR-camera is fed to a quantifier 13 having a plurality of outputs connected in parallel. In the illustrated embodiment the number of outputs is the same as the number of isotherms which are to be recorded, i.e. the number of outputs coincides with the number of quantifying steps. The incoming video signal is thus subdivided by the quantifier into a plurality of quantifying steps, and the signals representing the separate steps are each fed to an output of the quanitifier 13. Each such output is connected, via a switch 14 to an input of a shift register 15 having a parallel channels or paths with a length of $2^b$ bits. The outputs on the shift register 15 are each connected to a respective second input of the switch 14 which, under the control of a control unit 16, is switched between feeding the information coming to its first input on one of the parallel lines from the quantifier 13 to the input of the shift register, and the information coming to its second input from the output of the shift register. In the latter case the information in the shift register 15 circulates. The shift register 15 is stepped forward by clock pulses from the control unit 16. Any other type of suitable digital memory can naturally be used instead of a shift register, read-out and read-in being effected in a manner suitable in respect of the storage element chosen.

Each of the outputs of the shift register 15 is also connected to a respective amplifier 17–22. The amplifiers 17–22 have optional, variable amplification, which can be adjusted by a signal applied to a control input. The control inputs of the amplifiers 17–22 are connected to an amplification selector 23, which in turn is controlled by the control unit 16. The amplification selector 23 can be so designed, that according to a selected program and depending on the filter used it can set the amplification for each amplifier according to a scale graduated in five intervals, with completely damped amplification at one end and full amplification at the other. The settings selected for the filter in question are set by signals from the control unit 16.

Each of the outputs of the amplifiers 17–22 is connected to a respective input on an adder 24, which adds the incoming signals together to form a video signal, which is fed to an image forming unit 25, preferably in the form of a television monitor. In front of the screen of the image forming unit, there is a filter unit with a suitable filter 26, and the image is projected onto a camera 27.

The whole registering sequence is controlled by the control unit 16 in a manner such that after manual actuation the control unit first energizes the filter unit 26 to position the first filter in front of the screen and simultaneously energizes the amplification selector 23 to set the amplification of the necessary amplifiers 17–22 to the pre-selected amplification for the pertinent filter. Thereafter, the control unit 16 energizes the switch 14 to switch the quantifier outputs to the inputs of the shift register 15, and transmits clock signals to the shift register in response to a signal which provides an indication that a new image series is about to commence. The latter signal being obtained from a further circuit or from the quantifier. The shift register 15 is stepped forward to store the information from the quantifier 13. It should be noted that the signal on each output from the quantifier is of the "EITHER/OR" type, i.e. there is either a signal within the part-interval in question or not. This information is fed in at a rate determined by the clock signals from the control unit 16 on the control input of the shift register. Since information concerning a whole image area is to be stored in the shift register, the register in practice may comprise several units coupled in series.

When information for an entire image area has been fed into the shift register, the control unit sends a signal to the switch 14 instructing said switch to switch from input 1 to input 2, i.e. to connect the outputs 15 of the shift register to its inputs. The control unit 16 also energizes the image forming unit 25, and sends clock signals to the control input of the shift register for a whole sequence, the first image, corresponding to the filter which is in place in front of the screen, is displayed on the screen of the unit. The control unit 16 then energizes the camera 27 to take the first exposure of the image.

The control unit 16 thereafter sends a signal to the filter unit 26 instructing the same to change to a new filter, and instructs the amplification selector to change the amplification on the amplifiers 17-22 to conform to the filter now in place in front of the screen. The image forming unit 25 is then again activated and clock signals are sent to the shift register 15 for stepping forward a new sequence. The camera 27 makes a new exposure.

Subsequent thereto, the control unit 16 activates the filter unit 26 once again, such as to change to a new filter and the amplification selector to change the amplification of the amplifiers 17-22 to an amplification corresponding to this filter, and the last-mentioned sequence is then repeated.

Figure 7:
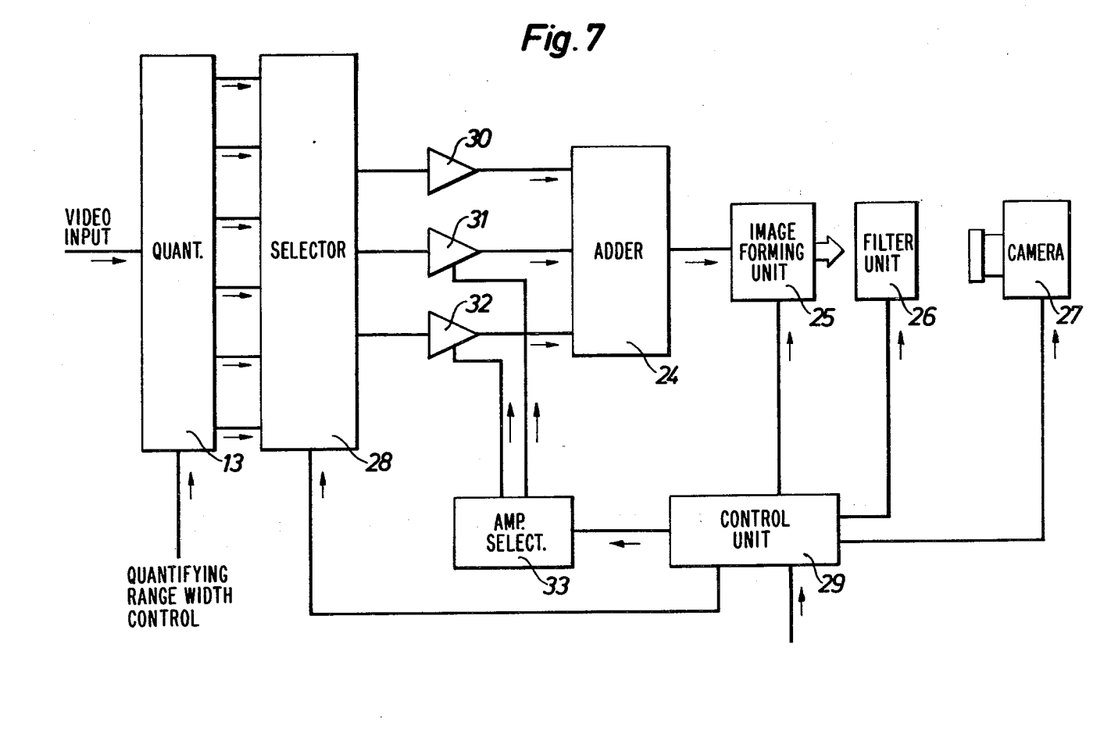

FIG. 7 illustrates a still further embodiment of a circuit for carrying out the embodiment of the method according to the invention described with reference to FIG. 4. The circuit illustrated in FIG. 7 can be used when the position of the object and its temperature are expected to remain the same for at least 3 seconds. In such a case, the video signal arriving from the camera need not be stored. This embodiment is based on the fact that not all the signals from all quantification steps are used with every image for every filter. As is apparent from FIG. 4, only the quantification steps for the temperatures between $T_1$ and $T_2$, $T_3$ and $T_4$, $T_5$ and $T_6$ need be received on the screen for exposure using a yellow filter. The same applies for exposures using red and blue filters, even if the quantification steps are other than those indicated in FIGS. 4d and 4e.

As a result of this, a selector 28 can be connected downstream of the quantifier 13, which in response to a signal from a control unit 29 selects the quantification steps applicable to the filter used for the exposure in question. Only as many amplifiers as selected quantification steps are needed, and in the case shown there are three amplifiers 30, 31 and 32. One of these can be operated at full amplification the whole time, while amplification of the other two can be varied with the aid of the amplification selector 33 controlled by the control unit 29. The remaining portions of the circuit have their counterpart in the circuit shown in FIG. 6, and the circuit in FIG. 7 is operated analogously to the circuit in FIG. 6.

A suitable number of so-called window-comparators connected in parallel can be used as quantifiers, for example. By controlling the upper and lower boundary levels of these comparators, variation of both the comparator range and the extent of each comparator range can be readily provided.

Many modifications are possible within the scope of the claims.

We claim:

1. A method of producing a color thermogram on a photographic color film starting from images, e.g., on a black and white television monitor screen, projected on the color film via color filters wherein at least two achromatic images are formed, said method comprising selecting the intensity of the achromatic color in each image to be a predetermined function of temperature and projecting each of the at least two images through one of a plurality of color filters providing a separate color for each image, so that the same portions of the image with achromatic colors conforming to the function selected for the different filters are projected through the different filters, whereby a picture is produced having hues varying between the colors represented by the different filters.

2. A method as claimed in claim 1, characterized in that the achromatic color intensity as a function of the temperature for each achromatic color image is a substantially continuous function.

3. A method as claimed in claim 2, characterized in that for each achromatic color image for each achromatic color, the achromatic functions have substantially the same configuration but cover different wavelength ranges and can be divided with different portions in different wavelength ranges, and wherein three color filters are used.

4. A method as claimed in claim 3, wherein said color filters are yellow, red and blue filters.

5. A method as claimed in claim 1 wherein to provide distinct colors for different isotherms, signal portions for several isotherms are obtained simultaneously from a video signal and amplified for each individual isotherm to a different extent in conformity with a given pattern, so that the selected isotherms generated on a television screen are given balanced achromatic colors, and that, for each generated image, the isotherms obtained are selected in conformity with a predetermined pattern for each image with balancing selected for each particular image.

6. An apparatus for producing a color thermogram on a photographic color film starting from images which are generated in an image forming unit such as a black and white television monitor screen and which are projected onto color film through color filters, said apparatus comprising a converter for receiving an incoming video signal and for converting the amplitude distribution of said incoming video signal so as to conform to that of at least two selectable intensity-temperature characteristics, a color filter device including a different color filter for each of said at least two characteristics and means for selectively placing a color filter for each characteristic between the image forming unit and the color film when the characteristic in question is selected so that the same parts of the image with achromatic colors conforming to those for the different intensity-temperature characteristics selected for the filters are projected through the different filters, whereby an image is obtained with hues varying between the colors represented by the different filters.

7. Apparatus as claimed in claim 6, characterized in that the converter comprises a plurality of function generators one for each said selected characteristic, and said apparatus including means for selectively connecting said function generators individually to the inputs of the image forming unit.

8. Apparatus as claimed in claim 6, for providing distinct colors for different isotherms, wherein said converter includes a quantifier having as many parallel outputs as the number of desired isotherms, and said apparatus further comprises a plurality of adjustable amplifiers connected to said outputs of said quantifier for proportionally varying each of the amplitudes of the output signals produced by the quantifier in accordance with said characteristics and an adder connected to the outputs of said plurality of amplifiers and having an output which is coupled to the input of the image forming unit.

9. Apparatus as claimed in claim 8, wherein the number of amplifiers is no greater than the greatest number of quantifying steps which are taken to provide any image on the image forming unit for any of the exposures, said apparatus further comprising a selector means connected between the quantifier and the amplifier for controllably connecting outputs of the quantifier to corresponding inputs of said amplifiers.

10. Apparatus as claimed in any of one of claims 6 to 9 further comprising an analog memory for storing the incoming video signal representing an entire image area, and means for providing reading of said memory once per exposure to generate signals for producing images on the image forming unit.

11. Apparatus as claimed in claim 8 or claim 9, wherein a digital memory is connected to the output of the quantifier so that output signals from the quantifier are written into said digital memory during the reception of a video signal relating to an entire image area and so that for each exposure, the information stored in the memory is read out and fed to the respective amplifiers, said information constituting the output signals from the quantifier.

12. Apparatus as claimed in claim 11, wherein said memory comprises a shift register with a plurality of parallel channels with selectable feedback outputs and with a plurality of inputs connected to the outputs of said quantifier, said apparatus further comprising means including switch means for selectively feeding back the signals from the outputs of the shift register to the inputs thereof and for providing that the sequence of stored signals in the shift register is arranged to circulate for one cycle in the shift register for each exposure required.

* * * * *